(12) United States Patent
Schulz et al.

(10) Patent No.: US 9,752,244 B2
(45) Date of Patent: Sep. 5, 2017

(54) GALVANIC NICKEL ELECTROPLATING BATH FOR DEPOSITING A SEMI-BRIGHT NICKEL

(71) Applicant: Atotech Deutschland GmbH, Berlin (DE)

(72) Inventors: Klaus-Dieter Schulz, Falkensee (DE); Philip Hartmann, Berlin (DE); Philipp Wachter, Berlin (DE); Mike Briese, Berlin (DE); Heiko Brunner, Berlin (DE); Richard Richter, Berlin (DE); Lars Kohlmann, Berlin (DE)

(73) Assignee: Atotech Deutschland GmbH, Berlin (DE)

( * ) Notice: Subject to any disclaimer, the term of this patent is extended or adjusted under 35 U.S.C. 154(b) by 0 days.

(21) Appl. No.: 14/421,568

(22) PCT Filed: Mar. 20, 2014

(86) PCT No.: PCT/EP2014/055649
§ 371 (c)(1),
(2) Date: Feb. 13, 2015

(87) PCT Pub. No.: WO2014/180595
PCT Pub. Date: Nov. 13, 2014

(65) Prior Publication Data
US 2016/0053395 A1    Feb. 25, 2016

(30) Foreign Application Priority Data
May 8, 2013  (EP) .................................. 13167074

(51) Int. Cl.
C25D 3/12    (2006.01)
C25D 3/18    (2006.01)
C25D 3/56    (2006.01)

(52) U.S. Cl.
CPC ............... C25D 3/562 (2013.01); C25D 3/18 (2013.01)

(58) Field of Classification Search
CPC .................................. C25D 3/18; C25D 3/562
USPC .......... 205/255, 259, 271, 279, 280
See application file for complete search history.

(56) References Cited

U.S. PATENT DOCUMENTS

| | | |
|---|---|---|
| 3,336,324 A | 8/1967 | Richter |
| 3,432,509 A | 3/1969 | Passal |
| 3,444,056 A | 5/1969 | Richter |
| 3,953,304 A * | 4/1976 | Allan .................. C07D 213/20 205/275 |
| 4,329,207 A | 5/1982 | Maruta |
| 5,951,841 A | 9/1999 | Wehlage et al. |
| 6,652,728 B1 * | 11/2003 | Sonntag ................ C25D 3/565 205/143 |
| 2005/0189231 A1 * | 9/2005 | Capper .................. C25D 3/565 205/246 |
| 2010/0155257 A1 * | 6/2010 | Brunner ............... C07D 213/82 205/246 |
| 2010/0300890 A1 | 12/2010 | Hartmann et al. |

FOREIGN PATENT DOCUMENTS

| | | | |
|---|---|---|---|
| DE | 1621157 | 5/1971 | |
| FR | 2292057 | 6/1976 | |
| FR | 2292057 A1 * | 6/1976 | ............... C25D 3/16 |
| JP | 2003027277 | 1/2003 | |
| JP | 2003293186 | 10/2003 | |

OTHER PUBLICATIONS

Anton et al., "Structure and Properties of Zwitterionic Polysoaps: Functionalization by Redox-Switchable Moieties," Progr Colloid Polym Sci (no month, 1992), vol. 89, pp. 56-59.*
Official Action for corresponding Japanese Patent Application No. 2015-515555 dated May 11, 2015.
PCT/EP2014/055649; PCT International Search Report and Written Opinion of the International Searching Authority dated Jun. 5, 2014.

* cited by examiner

Primary Examiner — Edna Wong
(74) Attorney, Agent, or Firm — Renner, Otto, Boisselle & Sklar, LLP

(57) ABSTRACT

The present invention is related to a galvanic nickel or nickel alloy electroplating bath for depositing a semi-bright nickel or nickel alloy coating characterized in that the electroplating bath comprises at least one compound having the general formula (I)

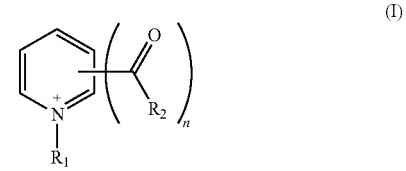

(I)

wherein $R_1=C_1-C_{18}$ hydrocarbon moiety substituted with a $SO_3^-$ group, $C_1-C_{18}$ hydrocarbon moiety substituted with a carboxylic group or $C_1-C_{18}$ hydrocarbon moiety substituted with at least an aromatic and/or a heteroaromatic group;
$R_2=NR_3R_4$ moiety, $OR_5$ moiety, or cyclic $NR_6$ moiety, wherein
$R_3$, $R_4$, $R_5$=hydrogen or $C_1-C_{18}$ hydrocarbon moiety or $C_1-C_{18}$ hydrocarbon moiety substituted with at least an aromatic and/or a heteroaromatic group, wherein $R_3$, $R_4$ and $R_5$ are identical or different;
$R_6=C_3-C_8$ hydrocarbon moiety or $C_3-C_8$ hydrocarbon moiety, wherein at least one carbon atom is substituted by a heteroatom; and
n=1-3.

16 Claims, No Drawings

GALVANIC NICKEL ELECTROPLATING BATH FOR DEPOSITING A SEMI-BRIGHT NICKEL

The present application is a U.S. National Stage Application based on and claiming benefit and priority under 35 U.S.C. §371 of International Application No. PCT/EP2014/055649, filed 20 Mar. 2014, which in turn claims benefit of and priority to European Application No. 13167074.7 filed 8 May 2013, the entirety of each of which is hereby incorporated herein by reference.

FIELD OF THE INVENTION

The present invention relates to a galvanic nickel or nickel alloy electroplating bath for depositing a semi-bright nickel or nickel alloy coating on an electrically conductive work piece; and a method therefore. The invention is further generally directed to the use of such a galvanic semi-bright nickel or nickel alloy electroplating bath for depositing a bright nickel or nickel alloy coating by conducting the method of the present invention. Additionally, the present invention claims absolute compound protection for the chemical compounds having the formulas (II), (III) and (IV).

BACKGROUND OF THE INVENTION

Bright nickel plating baths are used in the automotive, electrical, appliance, hardware and other industries. The most important functions of bright nickel plating are as an undercoating for chromium plating, helping finishers achieve a smooth bright finish and providing a significant amount of corrosion protection.

For decorative plated parts that need a high level of basis metal corrosion protection, semi-bright nickel deposits are almost always used in conjunction with subsequent deposits of bright nickel and chromium. The semi-bright nickel deposit is typically between about 60 and 70 percent of the total nickel deposited on the part, which offers the highest level of basis metal corrosion protection with the lowest total nickel thickness and the best appearance.

The most common nickel plating bath is a sulfate bath known as a Watts bath. In addition, in order to achieve bright and lustrous appearance of the nickel plating deposit, organic and inorganic agents (brighteners) are often added to the electrolyte. The types of added brighteners and their concentrations deter-mine the appearance of the nickel deposit, i.e., brilliant, bright, semi-bright, sat-in, etc.

Traditionally, coumarin has been used to obtain a high-leveling, ductile, semi-bright and sulfur-free nickel deposit from a Watts nickel bath. However, coumarin-free solutions are now available. A semi-bright nickel finish is semi-lustrous, as the name implies, but it was specifically developed for its ease of polishing and buffing. In the alternative, if subsequently bright nickel is plated, buffing can be eliminated. Brightness and smoothness are dependent on operating conditions.

One of the reasons that semi-bright nickel finishes are so easily buffed and/or polished is that the structure of the deposit is columnar, whereas the structure of a bright nickel finish is plate-like (lamellar). However, the structure of the deposit can be changed with various additives, a change in pH, current density or an increase in solution agitation, which is not a problem unless it affects properties of the deposit such as internal stress.

Internal stress of the plated nickel deposit can be compressive or tensile. Compressive stress is where the deposit expands to relieve the stress. In contrast, tensile stress is where the deposit contracts. Highly compressed deposits can result in blisters, warping or cause the deposit to separate from the substrate, while deposits with high tensile stress can also cause warping in addition to cracking and reduction in fatigue strength.

The use of coumarin as an additive in nickel electroplating baths, especially semi-bright nickel processes, to produce ductile, lustrous deposits with excellent leveling is well known. High concentrations of coumarin in the bath gives the best leveling results on one side, but such high coumarin concentrations also result on the other side in a high rate off formation of detrimental breakdown or degradation products. These degradation products are objectionable in that they can cause uneven, dull gray areas that are not easily brightened by a subsequent bright nickel deposit, they can reduce the leveling obtained from a given concentration of coumarin in the plating bath, and they can reduce the beneficial physical properties of the nickel deposits.

The use of various additives, such as formaldehyde and chloral hydrate has also been suggested to help overcome the undesirable effects of the coumarin degradation products. However, the use of such additives has certain limitations because even moderate concentrations of these materials not only increase the tensile stress of the nickel electrodeposits, but also significantly reduces the leveling action of the coumarin.

Even when since decades plating suppliers have proposed many bath formulations which claim to level as well as a coumarin bath, up to now, none of these baths formulations have met all of the necessary criteria.

As explained above, while the leveling of coumarin is exceptional coumarin has a disagreeable odor, breaks down and forms harmful degradation products, and these degradation products can only be removed by batch carbon treatments of the plating bath. These treatments are expensive and time consuming and normally must be done at least monthly and in some cases, even weekly.

DE 196 10 361 A1 discloses a process for a galvanic deposition of semi-bright nickel coatings on a substrate, wherein said substrate has been treated by an acidic aqueous galvanic bath comprising a cyclic N-allyl- or N-vinyl-ammonium compound, in particular based on pyridinium, as brightener additive.

However, none of the known prior art suggests a way to achieve the desired complex combination of good deposit properties of a semi-bright nickel or nickel alloy coating having good glance properties without generating high internal stress values. Prior art baths have solely been successful to achieve semi-bright nickel or nickel alloy coatings exhibiting some good properties while other properties have kept bad or turned bad, such a s combinations of good glance and high internal stress; or of bad glance and low internal stress.

OBJECTIVE OF THE PRESENT INVENTION

In view of the prior art, it was thus an object of the present invention to provide an amended galvanic nickel or nickel alloy electroplating bath for depositing a semi-bright nickel or nickel alloy coating on a substrate, which shall not exhibit the aforementioned shortcomings of the known prior art nickel electroplating baths.

In particular, it was an object of the present invention to provide an amended galvanic nickel or nickel alloy electroplating bath which shall be able for depositing a semi-bright nickel or nickel alloy coating on a plurality of different kind of substrates.

What is needed therefore is a way to deposit semi-bright nickel or nickel alloy coatings which possess good glance properties and a good leveling.

It is another object of the present invention to provide a coumarin-free semi-bright nickel or nickel alloy plating bath that approaches or even equals the leveling characteristics of a coumarin bath.

Furthermore, it was an object to provide a semi-bright nickel or nickel alloy coatings which possess low internal stress, in particular in combination with good glance properties.

Additionally, it was especially an object of the present invention to provide a semi-bright nickel or nickel alloy coatings which possess solely a minimum of cracks and pores in order to avoid undesired corrosion of metal surfaces if the substrate to be coated comprises metal, e.g. steel.

It is still another object of the present invention to provide a semi-bright nickel or nickel alloy plating bath that provides good stability over the life of the bath.

Further, it was an object of the present invention to provide an amended galvanic nickel or nickel alloy electroplating bath which shall be also suitable to be used for depositing bright nickel or nickel alloy coatings.

Further, it was an object of the present invention to provide an amended galvanic nickel or nickel alloy electroplating bath comprising a simple as possible general bath composition, preferably with chemicals as cheap as possible.

SUMMARY OF THE INVENTION

These objects and also further objects which are not stated explicitly but are immediately derivable or discernible from the connections discussed herein by way of introduction are achieved by a galvanic bath having features described in one embodiment. Appropriate modifications of the inventive galvanic bath are described in another embodiment. Further, an embodiment of the invention described herein comprises a method for depositing such a semi-bright nickel or nickel alloy coating on an electrically conductive work piece, while one embodiment comprises the use of such a galvanic semi-bright nickel or nickel alloy electroplating bath for depositing a bright nickel or nickel alloy coating by conducting such a method. A further embodiment of the invention comprises absolute chemical compound protection for the compounds having the formulas (II), (III), and (IV).

The present invention accordingly provides a galvanic nickel or nickel alloy electroplating bath for depositing a semi-bright nickel or nickel alloy coating characterized in that the electroplating bath comprises at least one compound having the general formula (I)

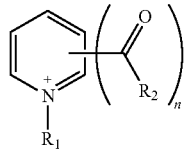
(I)

wherein $R_1 = C_1$-$C_{18}$ hydrocarbon moiety substituted with a $SO_3^-$ group, $C_1$-$C_{18}$ hydrocarbon moiety substituted with a carboxylic group or $C_1$-$C_{18}$ hydrocarbon moiety substituted with at least an aromatic and/or a heteroaromatic group;
$R_2 = NR_3R_4$ moiety, $OR_5$ moiety, or cyclic $NR_6$ moiety, wherein
$R_3$, $R_4$, $R_5$ = hydrogen or $C_1$-$C_{18}$ hydrocarbon moiety or $C_1$-$C_{18}$ hydrocarbon moiety substituted with at least an aromatic and/or a heteroaromatic group, wherein $R_3$, $R_4$ and $R_5$ are identical or different;
$R_6 = C_3$-$C_8$ hydrocarbon moiety or $C_3$-$C_8$ hydrocarbon moiety, wherein at least one carbon atom is substituted by a heteroatom; and
$n = 1$-$3$.

It is thus possible in an unforeseeable manner to provide an amended galvanic nickel or nickel alloy electroplating bath for depositing a semi-bright nickel or nickel alloy coating on a substrate, which does not exhibit the aforementioned shortcomings of the known prior art nickel electroplating baths.

In particular, the inventive amended galvanic nickel or nickel alloy electroplating bath is suitable for depositing a semi-bright nickel or nickel alloy coating on a plurality of different kind of substrates.

The present invention provides a coumarin-free semi-bright nickel or nickel alloy plating bath that at least approaches the leveling characteristics of a coumarin bath.

The achieved semi-bright nickel or nickel alloy coatings possess good glance properties and a good leveling.

Furthermore, the resulting semi-bright nickel or nickel alloy coatings possess low internal stress, in particular in combination with good glance properties.

Further, the present invention provides a semi-bright nickel or nickel alloy plating bath that provides good stability over the life of the bath.

Additionally, the obtained semi-bright nickel or nickel alloy coatings possess solely a minimum of cracks and pores whereby any undesired corrosion of a metal surface can be successfully avoided if the substrate to be coated comprises metal, e.g. steel.

Further, the inventive amended galvanic nickel or nickel alloy electroplating bath comprises a very simple general bath composition with mostly cheap single chemicals.

BRIEF DESCRIPTION OF THE TABLES

Objects, features, and advantages of the present invention will also become apparent upon reading the following description in conjunction with the tables, in which:

Table 1 exhibits experiments for semi-bright nickel coatings in accordance with embodiments of the present invention.

Table 2 exhibits experiments for semi-bright nickel coatings in accordance with comparative embodiments outside of the present invention.

Table 3 exhibits experiments for using semi-bright additives in accordance with embodiments of the present invention for bright nickel coatings.

DETAILED DESCRIPTION OF THE INVENTION

As used herein, the term "galvanic nickel or nickel alloy electroplating bath", when applied for depositing a semi-bright nickel or nickel alloy coating in accordance with the present invention, refers to a galvanic nickel bath, which is based on the so-called "Watts electrolytic bath", which has the general following composition:

| | |
|---|---|
| 240-550 g/l | nickel sulfate ($NiSO_4 \cdot 7H_2O$ or $NiSO_4 \cdot 6H_2O$), |
| 30-150 g/l | nickel chloride ($NiCl_2 \cdot 6H_2O$), and |
| 30-55 g/l | boric acid ($H_3BO_3$). |

The large amount of nickel sulfate provides the necessary concentration of nickel ions, while nickel chloride improves anode corrosion and increases conductivity. Boric acid is used as a weak buffer to maintain the pH value.

In the present invention, the galvanic nickel and nickel alloy electroplating baths have chloride content ranging from 10 to 50 g/l, preferably ranging from 15 to 40 g/l, and more preferably ranging from 20 to 30 g/l.

Nickel chloride may be replaced partly or entirely by sodium chloride.

Further, chloride in the electrolyte may be replaced partly or entirely by equivalent amounts of bromide.

Furthermore, the galvanic nickel bath may comprise in certain embodiments of the present invention at least a wetting agent, such as sodium salts of dihexyl sulfosuccinate, diamyl sulfosuccinate and/or 2-ethylhexylsulfate, wherein the concentration of such a wetting agent, is used, is ranging from 5 to 500 mg/l, preferably ranging from 10 to 350 mg/l, and more preferably ranging from 20 to 250 mg/l.

The cathodic current density amount to values ranging from 1 to 10 A/dm$^2$, preferably ranging from 2 to 7 A/dm$^2$, and more preferably ranging from 3 to 5 A/dm$^2$.

The galvanic nickel or nickel alloy electroplating bath of the present invention can be deposited on a plurality of different kind of substrates based on a metal and/or metal alloy, in particular steel, copper, brass and/or zinc diecasting; or on "POP" substrates. "POP" substrates mean in the sense of the invention plating on plastics. Thus, POP comprise a synthetic substrate, preferably based on at least one polymeric compound, more preferably based on acrylonitrile-butadiene-styrene (ABS), polyamide, polypropylene or ABS/PC (polycarbonate).

The expression n=1-3, 1 or 2, or 1 in general formula (I) of the present invention defines the number of substituents on the ring system of general formula (I). Thus, if n=3, the ring system of general formula (I) comprise three substituents, which can be arranged in ortho, meta and/or para position in relation to the nitrogen atom of the ring system following hereby the general known substitution rules of organic chemistry. Conclusively, if n=2, there are two of such substituents; while if n=1, there is solely one such substituent on the ring system present.

Electrolytes for obtaining matte nickel or nickel alloy deposits, by contrast, do not form part of this invention.

In one embodiment, the electroplating bath further comprises an alkali metal, preferably sodium, benzoate at a concentration ranging from 0.005 to 5 g/l, preferably from 0.02 to 2 g/l, more preferably from 0.05 to 0.5 g/l. Such additive compounds help to reduce internal stress of the deposited coatings.

In one embodiment, the electroplating bath further comprises salicylic acid at a concentration ranging from 0.1 to 10 g/l, preferably from 0.3 to 6 g/l, more preferably from 0.5 to 3.5 g/l. Such an additive affects positively the hardness, durability and the optical properties of the achieved coatings.

In a preferred embodiment, the electroplating bath comprises at least one compound having the general formula (I), wherein $R_1$=$C_1$-$C_8$, preferably $C_1$-$C_4$, hydrocarbon moiety substituted with a $SO_3^+$ group, $C_1$-$C_8$, preferably $C_1$-$C_4$, hydrocarbon moiety substituted with a carboxylic group or $C_1$-$C_8$, preferably $C_1$-$C_4$, hydrocarbon moiety substituted with at least an aromatic and/or a heteroaromatic group;
$R_2$=$NR_3R_4$ moiety, $OR_5$ moiety, or cyclic $NR_6$ moiety, wherein
$R_3$, $R_4$, $R_5$=hydrogen or $C_1$-$C_{18}$ hydrocarbon moiety or $C_1$-$C_{18}$ hydrocarbon moiety substituted with at least an aromatic and/or a heteroaromatic group, wherein $R_3$, $R_4$ and $R_5$ are identical or different;
$R_6$=$C_4$-$C_8$ hydrocarbon moiety or $C_3$-$C_8$ hydrocarbon moiety, wherein at least one carbon atom is substituted by a heteroatom; and
n=1 or 2.

In another preferred embodiment, the electroplating bath comprises at least one compound having the general formula (I), wherein
$R_1$=$C_1$-$C_8$, preferably $C_1$-$C_4$, hydrocarbon moiety substituted with a $SO_3^-$ group, $C_1$-$C_8$, preferably $C_1$-$C_4$, hydrocarbon moiety substituted with a carboxylic group or $C_1$-$C_8$, preferably $C_1$-$C_4$, hydrocarbon moiety substituted with at least an aromatic and/or a heteroaromatic group;
$R_2$=$NR_3R_4$ moiety, $OR_5$ moiety, or cyclic $NR_6$ moiety, wherein
$R_3$, $R_4$, $R_5$=hydrogen or $C_1$-$C_8$, preferably $C_1$-$C_4$, hydrocarbon moiety or $C_1$-$C_8$, preferably $C_1$-$C_4$, hydrocarbon moiety substituted with at least an aromatic and/or a heteroaromatic group, wherein $R_3$, $R_4$ and $R_5$ are identical or different;
$R_6$=$C_4$ or $C_5$ hydrocarbon moiety or $C_4$-$C_5$ hydrocarbon moiety, wherein at least one carbon atom is substituted by a sulfur or oxygen atom; and
n=1.

In a more preferred embodiment, the electroplating bath comprises at least one compound having the general formula (I), wherein
$R_1$=n-ethyl-$SO_3^-$, n-propyl-$SO_3^-$, n-butyl-$SO_3^-$, benzyl, $CH_2$—COOH or a salt thereof, preferably the sodium salt $CH_2$—COONa, moiety;
$R_2$=$NH_2$, N(ethyl)$_2$, O(ethyl), OH moiety, or cyclic $NR_6$ moiety, wherein
$R_6$=$C_4$ or $C_5$ hydrocarbon moiety or $C_4$-$C_5$ hydrocarbon moiety, wherein at least one carbon atom is substituted by a sulfur or an oxygen atom; and
n=1.

In one embodiment, the electroplating bath comprises at least one compound having the general formula (I), wherein $R_1$ is not hydrogen.

In one embodiment, the working temperature ranges from 40° C. to 70° C., preferably from 45° C. to 65° C., more preferably from 50° C. to 60° C.

In one embodiment, the electroplating bath comprises the at least one compound having the general formula (I) at a concentration ranging from 0.005 to 10 g/l, preferably from 0.008 to 5 g/l, more preferably from 0.01 to 1 g/l.

In one embodiment, the at least one moiety $C(O)R_2$ is in ortho, meta and/or para position at the aromatic ring.

In one embodiment, the electroplating bath further comprises chloral hydrate at a concentration ranging from 0.005 to 5 g/l, preferably from 0.02 to 2 g/l, more preferably from 0.05 to 0.5 g/l. Such an additive helps to set up the potential and serves further to amend the glance properties and the throwing power of the deposited coatings.

In one embodiment, the electroplating bath further comprises at least one compound selected from brighteners, leveling agents, internal stress reducers, and wetting agents, in particular at a concentration ranging from 0.005 to 5 g/l, preferably from 0.02 to 2 g/l, more preferably from 0.05 to 0.5 g/l.

In one embodiment, the pH-Value of the electroplating bath ranges from 2 to 6, preferably from 3 to 5, more preferably from 3.5 to 4.6.

In one embodiment, the electroplating bath comprises additionally at least one bright nickel additive, preferably PPS and/or PPS-OH, which is, if used without at least one compound having the general formula (I), unsuitable for depositing semi-bright nickel deposits. The concentration ratio between the at least one additional bright nickel additive, such as PPS and/or PPS-OH, and the at least one compound having the general formula (I) is less than 10:1, preferably less than 5:1, and more preferably less than 3:1; wherein each of the at least one compound having the general formula (I) and the at least one additional bright nickel additive have a concentration ranging from 0.005 to 10 g/l, preferably from 0.008 to 5 g/l, and more preferably from 0.01 to 1 g/l.

This offers a tremendous advantage by being able to substitute large quantities of expensive compounds having formula (I) by cheap known bright nickel additives, such as PPS and/or PPS-OH, without that the known disadvantages of PPS and PPS-OH occur.

Further, the object of the present invention is also solved by a method for depositing a semi-bright nickel or nickel alloy coating on an electrically conductive work piece, comprising the following method steps:

i) Bringing the work piece into contact with a semi-bright nickel or nickel alloy electroplating bath according to the present invention;

ii) Bringing at least one anode into contact with the semi-bright nickel or nickel alloy electroplating bath;

iii) Applying a voltage across the work piece and the at least one anode; and iv) Electrodepositing a semi-bright nickel or nickel alloy coating on the work piece.

Additionally, the object of the present invention is also solved by making use of such a galvanic semi-bright nickel or nickel alloy electroplating bath for depositing a bright nickel or nickel alloy coating by conducting such a method, wherein additionally a primary brightener is added to the semi-bright nickel or nickel alloy electroplating bath.

Such a primary brightener can comprise unsaturated, in most cases aromatic sulfonic acids, sulfonamides, sulfimides, N-sulfonylcarboxamides, sulfinates, diarylsulfones or the salts thereof, in particular the sodium or potassium salts.

The most familiar compounds are for example m-benzenedisulfonic acid, benzoic acid sulfimide (saccharine), trisodium 1,3,6-naphthalene trisulfonate, sodium benzene monosulfonate, dibenzene sulfonamide, sodium benzene monosulfinate, vinyl sulfonic acid, allyl sulfonic acid, sodium salt of allyl sulfonic acid, p-toluene sulfonic acid, p-toluene sulfonamide, sodium propargyl sulfonate, benzoic acid sulfimide, 1,3,6-naphthalenetrisulfonic acid and benzoyl benzene sulfonamide.

Further, such a primary brightener can comprise propargyl alcohol and/or derivatives thereof.

The primary brighteners can be employed and added to the electrolyte bath at a concentration ranging from 0.001 to 8 g/l, preferably from 0.01 to 2 g/l, more preferably from 0.02 to 1 g/l. It is also possible to use several primary brighteners simultaneously.

It has been surprisingly found in the context of the present invention, that new and inventive chemical compounds could be synthesized, which have been absolutely unknown up to now.

Further, the present invention claims absolute compound protection for the chemical compounds having the following formulas (II), (III) and (IV):

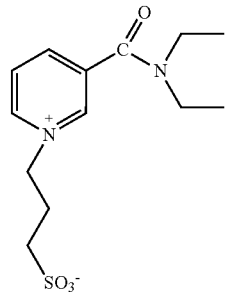

(II)

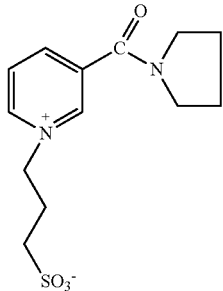

(III)

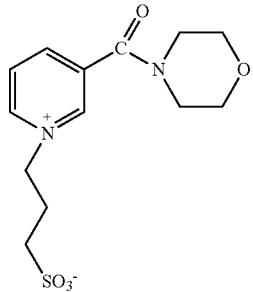

(IV)

In order to fulfill a sufficient disclosure of these absolute new chemical compounds, there will be given their synthesis procedures in the following:

3-(3-(Diethylcarbamoyl)pyridinium-1-yl)propan-1-sulfonate (II)

10 g (0.0555 mol) of nicotinic acid diethylamide (99%) are dissolved in 50 ml of ethanol. Subsequently 6.78 g (0.0555 mol) of 1,3-propane sultone are added. Then, the reaction mixture is cooked under reflux for 48 hours at 78° C.

After finishing of the reaction, the reaction mixture is cooled before 100 ml of diethyl ether are added at room temperature. The resulting white solid is filtered at 4° C., washed with additional 100 ml of diethyl ether, and finally vacuum dried.

9.00 g of a white solid is yielded (54% of theory).

3-(3-(pyrrolidin-1-carbonyl)pyridinium-1-yl) propane-1-sulfonate (III)

10 g (0.056747 mol) of 3-(pyrrolidin-1-carbonyl)pyridine are dissolved in 50 ml of ethanol. Subsequently 6.93 g (0.056747 mol) of 1,3-propane sultone are added. Then, the reaction mixture is cooked under reflux for 48 hours at 78° C.

After finishing of the reaction, the reaction mixture is cooled before 100 ml of diethyl ether are added at room temperature. The resulting white solid is filtered at 4° C., washed with additional 100 ml of diethyl ether, and finally vacuum dried.

8.635 g of a white solid is yielded (51% of theory).

3-(3-(morpholin-4-carbonyl)pyridinium-1-yl) propane-1-sulfonate (IV)

10 g (0.05206 mol) of 3-(morpholine-1-carbonyl)pyridine are dissolved in 50 ml of ethanol. Subsequently 6.36 g (0.05206 mol) of 1,3-propane sultone are added. Then, the reaction mixture is cooked under reflux for 48 hours at 78° C.

After finishing of the reaction, the reaction mixture is cooled before 100 ml of diethyl ether are added at room temperature. The resulting white solid is filtered at 4° C., washed with additional 100 ml of diethyl ether, and finally vacuum dried.

8.10 g of a white solid is yielded (49.5% of theory).

The present invention thus addresses the problem of providing an amended galvanic nickel or nickel alloy electroplating bath for depositing a semi-bright nickel or nickel alloy coating on a plurality of a different kind of substrates. The inventive electrolytic bath offers a way to achieve semi-bright nickel or nickel alloy coatings having a good and unique combination of desired properties, such as glance, leveling, ductility and so on, whereas known prior art baths can solely provide some of these properties, wherein at least one severe disadvantage in form of a bad underside property is present. The inventive baths offers par example on steel the desired property combination of having a good leveling, a low hardness and a high ductility; and on POP's the combination of a good glance and simultaneously low internal stress values.

The following non-limiting examples are provided to illustrate an embodiment of the present invention and to facilitate understanding of the invention, but are not intended to limit the scope of the invention, which is defined by the claims appended hereto.

In general, there has to be mentioned, that all experiments, comprising the experiments in accordance with the present invention as well as the comparative embodiments outside of the present invention, has been conducted using a so-called "Watts electrolytic bath" having the following composition:

| 280 g/l | nickel sulfate (NiSO$_4$•7H$_2$O), |
| 35 g/l | nickel chloride (NiCl$_2$•6H$_2$O), |
| 35 g/l | boric acid (H$_3$BO$_3$). and |
| 50 mg/l | sodium dihexyl sulfosuccinate. |

Further, at least one compound having the general formula (I) of the present invention was added to the above-cited basic Watts electrolytic bath.

The nickel deposition took place in a Hull cell wherein 2.5 Ampere was applied for 10 minutes at a temperature of 55° C.+/−3° C. Further, 3 liter/min pressure air was introduced during nickel deposition.

The substrates have been pretreated in the following manner before their use for the nickel deposition:
 i) Degreasing by hot soak cleaner
 ii) Electrolytic degreasing
 iii) Rinsing,
 iv) Acid dipping with 10 vol % sulfuric acid Sample substrates, made of copper and brass, have been scratched for subjective optical judgment of leveling. The glance of the resulting nickel deposits on the substrates has been also judged optically.

All results shown in Tables 1, 2 and 3 for leveling, glance and internal stress are qualitatively ranked having the following synonyms:

| +++ | Excellent |
| ++ | Good |
| + | Medium |
| − | Bad |

In case of internal stress excellent means very low stress or in ideal case no internal stress.

All concentrations given in Tables 1, 2 and 3 for the compound having formula (I) as well as for the different further bath components are listed in mg/l, if not stated differently. The basic electrolytic bath components (Watts's bath) are listed above and will not be repeated in the Tables, even if they are of course comprised. Golpanol BMP (2-butyne-1,4-diol propoxylate) is a commercially available brightener.

The experiments given in Tables 1, 2 and 3 are numbered in consequent order wherein the second number in parentheses is an internal experiment number of the applicant.

The expression n=1 (meta) in the column "Additive" par example means that there is one substituent C(O)R$_2$ on the ring system, which is positioned in meta position relating to the nitrogen atom of the ring system.

Turning now to the Tables, Table 1 shows conducted experiments for semi-bright nickel coatings in accordance with embodiments of the present invention.

TABLE 1

Experiments for semi-bright nickel coatings

| Exp. | Additive | Conc | Bath | Leveling | Glance | Stress |
|---|---|---|---|---|---|---|
| 1 (37) | n = 1 (meta) R$_2$ = N(Ethyl)$_2$ R$_1$ = (CH$_2$)$_3$SO$_3^-$ | 100 | No further additives | +++ | + | +++ |
| 2 (37) | n = 1 (meta) R$_2$ = N(Ethyl)$_2$ R$_1$ = (CH$_2$)$_3$SO$_3^-$ | 100 | 75 Chloral hydrate | +++ | ++ | +++ |
| 3 (38) | n = 1 (para) R$_2$ = N(Ethyl)$_2$ R$_1$ = (CH$_2$)$_3$SO$_3^-$ | 100 | 75 Chloral hydrate | +++ | ++ | +++ |
| 4 (39) | n = 1 (ortho) R$_2$ = N(Ethyl)$_2$ R$_1$ = (CH$_2$)$_3$SO$_3^-$ | 100 | 75 Chloral hydrate | +++ | +++ | ++ |

TABLE 1-continued

Experiments for semi-bright nickel coatings

| Exp. | Additive | Conc | Bath | Leveling | Glance | Stress |
|---|---|---|---|---|---|---|
| 5 (54) | $n = 1$ (meta) $R_2 = NH_2$ $R_1 = (CH_2)_3SO_3^-$ | 200 | 75 Chloral hydrate, 300 Na-benzoate | +++ | ++ | +++ |
| 6 (46) | $n = 1$ (meta) $R_2 = OH$ $R_1 = (CH_2)_3SO_3^-$ | 200 | 75 Chloral hydrate, 300 Na-benzoate | ++ | + | +++ |
| 7 (27) | $n = 1$ (meta) $R_2 = NH_2$ $R_1 = CH_2COONa$ and $Cl^-$ | 100 | 75 Chloral hydrate, 75 Golpanol, 200 Na-benzoate | ++ | ++ | +++ |
| 8 (53) | $n = 1$ (meta) $R_2 = OH$ $R_1 = CH_2COONa$ and $Cl^-$ | 200 | 75 Chloral hydrate, 300 Na-benzoate | + | + | ++ |
| 9 (34) | $n = 1$ (meta) $R_2 = N(Ethyl)_2$ $R_1 =$ benzyl and $Cl^-$ | 20 | 75 Chloral hydrate | ++ | + | ++ |
| 10 (57) | $n = 1$ (meta) $R_2 = N(Ethyl)_2$ $R_1 = (CH_2)_2SO_3Na$ and $Br^-$ | 200 | 75 Chloral hydrate, 300 Na-benzoate | +++ | ++ | +++ |
| 11 (58) | $n = 1$ (meta) $R_2 = N(Ethyl)_2$ $R_1 = (CH_2)_4SO_3^-$ | 200 | 75 Chloral hydrate, 300 Na-benzoate | +++ | ++ | +++ |
| 12 (59-1) | $n = 1$ (meta) $R_2 = $O-Ethyl $R_1 = (CH_2)_3SO_3^-$ | 200 | 75 Chloral hydrate, 300 Na-benzoate | + | + | ++ |
| 13 (59-2) | $n = 1$ (meta) $R_2 = $O-Ethyl $R_1 = (CH_2)_3SO_3^-$ | 400 | 75 Chloral hydrate, 300 Na-benzoate | +++ | ++ | ++ |
| 14 (37) | $n = 1$ (meta) $R_2 = N(Ethyl)_2$ $R_1 = (CH_2)_3SO_3^-$ | 100 | 75 Chloral hydrate, 100 PPS, 300 Na-benzoate | +++ | ++ | ++ |
| 15 (37) | $n = 1$ (meta) $R_2 = N(Ethyl)_2$ $R_1 = (CH_2)_3SO_3^-$ | 80 | 260 Chloral hydrate, 34 butane diol, 2500 salicylic acid, 140 hexindiol, 12 Golpanol BMP | ++ | ++ | ++ |
| 16 (166) | Formula (IV) [see claim 15] | 100 | 75 Chloral hydrate | ++ | ++ | ++ |
| 17 (167) | Formula (III) [see claim 15] | 100 | 75 Chloral hydrate | ++ | ++ | + |

Table 2 exhibits experiments for semi-bright nickel coatings in accordance with comparative embodiments outside of the present invention wherein known examples of the semi-bright nickel coatings have been chosen, such as PPS and PPS-OH (experiments 19 and 20).

The comparative experiments exhibit often good results due to internal stress and leveling, but at the same time glance values are bad. This discrepancy is typical for known prior art systems in the semi-bright nickel coating industry as described before.

TABLE 2

Comparative experiments for semi-bright nickel coatings

| Exp. | Additive | Conc | Bath | Leveling | Glance | Stress |
|---|---|---|---|---|---|---|
| 18 | None | — | 260 Chloral hydrate, 34 butane diol, 2500 salicylic acid, 140 hexindiol, 12 Golpanol BMP | – | – | – |
| 19 (55) | No substituent PPS $R_1 = (CH_2)_3SO_3^-$ | 200 | 75 Chloral hydrate, 300 Na-benzoate | + | – | +++ |
| 20 (56) | No substituent PPS-OH $R_1 = CH_2CH(OH)CH_2SO_3^-$ | 200 | 75 Chloral hydrate, 300 Na-benzoate | + | – | ++ |
| 21 (18) | No substituent $R_1 = CH_2COOH$ and $Cl^-$ | 100 | 75 Chloral hydrate | ++ | – | – |

TABLE 2-continued

Comparative experiments for semi-bright nickel coatings

| Exp. | Additive | Conc | Bath | Leveling | Glance | Stress |
|---|---|---|---|---|---|---|
| 22 (30) | No substituent $R_1 = CH_2CH(OH)CH_2OH$ and $Cl^-$ | 100 | 75 Chloral hydrate | ++ | − | ++ |
| 23 (31) | No substituent $R_1 = C_6H_6{-}COOH$ and $Cl^-$ | 100 | 75 Chloral hydrate | + | − | ++ |
| 24 | N-allyl pyridinium chloride DE19610361A1 | 100 | 75 Chloral hydrate | − | − | − |

A special surprising effect of a preferred embodiment of the present invention shall be outlined by a direct comparison of experiments 2, 14 and 19, wherein in experiment 19 no inventive additive has been added whereas in experiments 2 and 14 the same inventive additive has been added, once without additional PPS (experiment 2) and once with additional PPS in combination (experiment 14). But, the achieved nickel coatings have similar qualities as can be easily seen above, even if PPS alone (experiment 19) is not suitable for achieving good semi-bright nickel coatings. This highlights the capabilities of the inventive additives having general formula (I) that they are not solely able to generate good semi-bright nickel coatings, but also that they can be mixed and/or at least partially substituted by known cheap bright nickel additives, such as PPS and/or PPS-OH, without losing their brilliant coating qualities. This makes a possible commercial application even more promising. The same inventive effect is shown by comparing experiments 15 and 18, wherein salicylic acid has been used as known additive for bright nickel baths.

Table 3 exhibits experiments for using inventive semi-bright additives of the present invention for generating bright nickel coatings.

TABLE 3

Experiments for using semi-bright additives of the present invention for bright nickel coatings

| Exp. | Additive | Conc | Bath | Leveling | Glance | Stress |
|---|---|---|---|---|---|---|
| 25 (37) | n = 1 (meta) $R_2 = N(Ethyl)_2$ $R_1 = (CH_2)_3SO_3^-$ | 200 | 10 Propargyl alcohol 10 Na-propargylsulfonate 800 Na-allylsulfonate 4 g/l Na-saccharine | +++ | +++ | +++ |
| 26 (38) | n = 1 (para) $R_2 = N(Ethyl)_2$ $R_1 = (CH_2)_3SO_3^-$ | 200 | 10 Propargyl alcohol 10 Na-propargylsulfonate 800 Na-allylsulfonate 4 g/l Na-saccharine | +++ | +++ | +++ |
| 27 (39) | n = 1 (ortho) $R_2 = N(Ethyl)_2$ $R_1 = (CH_2)_3SO_3^-$ | 200 | 10 Propargyl alcohol 10 Na-propargylsulfonate 800 Na-allylsulfonate 4 g/l Na-saccharine | +++ | +++ | +++ |

Thus, the inventive additives can be also successfully used for generating bright nickel coatings by adding primary brighteners and/or by using other typical prior art bath components for bright nickel coatings. The bright coatings of experiments 18, 19 and 20 exhibited glance ranging from 0 (HCD) to 9.5 cm (LCD).

While the principles of the invention have been explained in relation to certain particular embodiments, and are provided for purposes of illustration, it is to be understood that various modifications thereof will become apparent to those skilled in the art upon reading the specification. Therefore, it is to be understood that the invention disclosed herein is intended to cover such modifications as fall within the scope of the appended claims. The scope of the invention is limited only by the scope of the appended claims.

The invention claimed is:

1. Galvanic nickel electroplating bath for depositing a semi-bright nickel coating characterized in that the electroplating bath comprises at least one compound having the general formula (I)

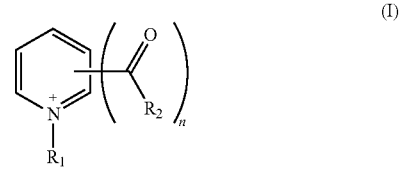

wherein $R_1 = C_1{-}C_{18}$ hydrocarbon moiety substituted with a $SO_3^-$ group or $C_1{-}C_4$ hydrocarbon moiety substituted with a carboxylic group, or a salt thereof;

$R_2 = NR_3R_4$ moiety, $OR_5$ moiety, or cyclic $NR_6$ moiety, wherein $R_3$, $R_4$, $R_5$=hydrogen or $C_1{-}C_{18}$ hydrocarbon moiety or $C_1{-}C_{18}$ hydrocarbon moiety substituted with at least an aromatic and/or a heteroaromatic group, wherein $R_3$, $R_4$ and $R_5$ are identical or different;

$R_6 = C_3{-}C_8$ hydrocarbon moiety or $C_3{-}C_8$ hydrocarbon moiety, wherein at least one carbon atom is substituted by a heteroatom; and n=1-3, and wherein the pH-value of the electroplating bath ranges from 2 to 6.

2. Galvanic nickel electroplating bath according to claim 1 characterized in that the electroplating bath further comprises an alkali metal or ammonium benzoate at a concentration ranging from 0.005 to 5 g/l.

3. Galvanic nickel electroplating bath according to claim 1 characterized in that the electroplating bath comprises at least one compound having the general formula (I), wherein
$R_1=C_1-C_8$ hydrocarbon moiety substituted with a $SO_3^-$ group or $C_1-C_4$ hydrocarbon moiety substituted with a carboxylic group;
$R_2=NR_3R_4$ moiety, $OR_5$ moiety, or cyclic $NR_6$ moiety, wherein $R_3$, $R_4$, $R_5$=hydrogen or $C_1-C_{18}$ hydrocarbon moiety or $C_1-C_{18}$ hydrocarbon moiety substituted with at least an aromatic and/or a heteroaromatic group, wherein $R_3$, $R_4$ and $R_5$ are identical or different;
$R_6=C_4-C_8$ hydrocarbon moiety or $C_3-C_8$ hydrocarbon moiety, wherein at least one carbon atom is substituted by a heteroatom; and
$n=1$ or $2$.

4. Galvanic nickel electroplating bath according to claim 1 characterized in that the electroplating bath comprises at least one compound having the general formula (I), wherein
$R_1=C_1-C_8$ hydrocarbon moiety substituted with a $SO_3^-$ group or $C_1-C_4$ hydrocarbon moiety substituted with a carboxylic group;
$R_2=NR_3R_4$ moiety, $OR_5$ moiety, or cyclic $NR_6$ moiety, wherein $R_3$, $R_4$, $R_5$=hydrogen or $C_1-C_8$, hydrocarbon moiety or $C_1-C_8$, hydrocarbon moiety substituted with at least an aromatic and/or a heteroaromatic group, wherein $R_3$, $R_4$ and $R_5$ are identical or different;
$R_6=C_4$ or $C_5$ hydrocarbon moiety or $C_4-C_5$ hydrocarbon moiety, wherein at least one carbon atom is substituted by a sulfur or oxygen atom; and
$n=1$.

5. Galvanic nickel electroplating bath according to claim 1 characterized in that the electroplating bath comprises at least one compound having the general formula (I), wherein
$R_1$=n-ethyl-$SO_3^-$, n-propyl-$SO_3^-$, n-butyl-$SO_3^-$, $CH_2$—COOH or a salt thereof, moiety;
$R_2=NH_2$, N(ethyl)$_2$, O(ethyl), OH moiety, or cyclic $NR_6$ moiety, wherein $R_6=C_4$ or $C_5$ hydrocarbon moiety or $C_4-C_5$ hydrocarbon moiety, wherein at least one carbon atom is substituted by a sulfur or an oxygen atom; and
$n=1$.

6. Galvanic nickel electroplating bath according to claim 1 characterized in that the working temperature ranges from 40° C. to 70° C.

7. Galvanic nickel electroplating bath according to claim 1 characterized in that the electroplating bath comprises the at least one compound having the general formula (I) at a concentration ranging from 0.005 to 10 g/l.

8. Galvanic nickel electroplating bath according to claim 1 characterized in that the at least one moiety $C(O)R_2$ is in ortho, meta and/or para position at the aromatic ring.

9. Galvanic nickel electroplating bath according to claim 1 characterized in that the electroplating bath further comprises chloral hydrate at a concentration ranging from 0.005 to 5 g/l.

10. Galvanic nickel electroplating bath according to claim 1 characterized in that the electroplating bath further comprises at least one compound selected from brighteners, leveling agents, internal stress reducers, and wetting agents, at a concentration ranging from 0.001 to 8 g/l.

11. Galvanic nickel electroplating bath according to claim 1 characterized in that the electroplating bath comprises additionally at least one bright nickel additive which is, if used without at least one compound having the general formula (I), unsuitable for depositing semi-bright nickel deposits.

12. Galvanic nickel electroplating bath according to claim 1 characterized in that $R_1=CH_2$—COOH or a salt thereof.

13. Galvanic nickel electroplating bath according to claim 1 characterized in that $R_1=C_1-C_4$ hydrocarbon moiety substituted with a $SO_3^-$ group.

14. Method for depositing a semi-bright nickel coating on an electrically conductive work piece comprising the following method steps:
i) bringing the work piece into contact with the galvanic nickel electroplating bath according to claim 1;
ii) bringing at least one anode into contact with the galvanic nickel electroplating bath;
iii) applying a voltage across the work piece and the at least one anode; and
iv) electrodepositing a semi-bright nickel coating on the work piece.

15. A process for depositing a bright nickel coating, comprising the following method steps:
i) bringing the work piece into contact with the galvanic nickel electroplating bath according to claim 1, wherein additionally a primary brightener is added to the galvanic nickel electroplating bath;
ii) bringing at least one anode into contact with the galvanic nickel electroplating bath;
iii) applying a voltage across the work piece and the at least one anode; and
iv) electrodepositing a bright nickel coating on the work piece.

16. Galvanic nickel electroplating bath for depositing a semi-bright nickel coating characterized in that the electroplating bath comprises at least one compound having the general formula (I)

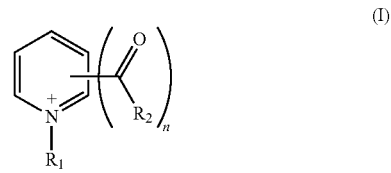

(I)

wherein $R_1=C_1-C_4$ hydrocarbon moiety substituted with a $SO_3^-$ group or $CH_2$—COOH or a salt thereof;
$R_2=NR_3R_4$ moiety, $OR_5$ moiety, or cyclic $NR_6$ moiety, wherein $R_3$, $R_4$, $R_5$=hydrogen or $C_1-C_{18}$ hydrocarbon moiety or $C_1-C_{18}$ hydrocarbon moiety substituted with at least an aromatic and/or a heteroaromatic group, wherein $R_3$, $R_4$ and $R_5$ are identical or different;
$R_6=C_3-C_8$ hydrocarbon moiety or $C_3-C_8$ hydrocarbon moiety, wherein at least one carbon atom is substituted by a heteroatom; and
$n=1-3$.

* * * * *